(12) United States Patent
Steen et al.

(10) Patent No.: US 6,213,995 B1
(45) Date of Patent: Apr. 10, 2001

(54) FLEXIBLE TUBING WITH BRAIDED SIGNAL TRANSMISSION ELEMENTS

(75) Inventors: Brett Steen, Ooltewah, TN (US); Stevie Daniel, Trenton, GA (US)

(73) Assignee: Phelps Dodge High Performance Conductors of SC and GA, Inc., Inman, SC (US)

( * ) Notice: Subject to any disclaimer, the term of this patent is extended or adjusted under 35 U.S.C. 154(b) by 0 days.

(21) Appl. No.: 09/387,528

(22) Filed: Aug. 31, 1999

(51) Int. Cl.$^7$ ................................................ A61M 25/00
(52) U.S. Cl. ................................................ 604/527
(58) Field of Search ................................ 138/123, 140, 138/141; 607/132, 115, 111, 122; 604/20, 21, 284, 523–527, 529, 265, 266

(56) References Cited

U.S. PATENT DOCUMENTS

| | | | |
|---|---|---|---|
| 3,485,234 | 12/1969 | Stevens | 128/2 |
| 3,585,707 | 6/1971 | Stevens | 29/427 |
| 3,924,632 | 12/1975 | Cook | 128/348 |
| 4,484,586 | 11/1984 | McMickle et al. | 128/786 |
| 4,665,604 | 5/1987 | Dubowik | 29/415 |
| 4,900,314 | 2/1990 | Quackenbush | 604/282 |
| 5,052,105 | 10/1991 | Mische et al. | 29/883 |
| 5,057,092 | * 10/1991 | Webster, Jr. . | |
| 5,247,136 | 9/1993 | Mitsuyasu et al. | 174/113 R |
| 5,275,152 | * 1/1994 | Krauter et al. | 128/4 |
| 5,334,169 | 8/1994 | Brown et al. . | |
| 5,496,292 | * 3/1996 | Burnham | 604/282 |
| 5,514,236 | 5/1996 | Avellanet et al. | 156/154 |
| 5,591,142 | * 1/1997 | Van Erp . | |
| 5,630,806 | * 5/1997 | Inagaki et al. . | |
| 5,702,373 | 12/1997 | Samson | 604/282 |
| 5,755,704 | 5/1998 | Lunn | 604/282 |
| 5,792,401 | * 8/1998 | Burnham | 264/103 |
| 5,928,279 | * 7/1999 | Shannon et al. | 623/1 |
| 6,017,335 | * 1/2000 | Burnham | 604/282 |

\* cited by examiner

Primary Examiner—Sharon Kennedy
(74) Attorney, Agent, or Firm—David P. Gordon; David S. Jacobson; Thomas A Gallagher

(57) ABSTRACT

A flexible tubing includes a wall provided with a plurality of braided elements forming a braid within the wall of the tube. The braided elements include one or more signal transmitting elements and one or more metallic or non-metallic structural elements having structural properties different from the signal transmitting elements. The signal transmitting elements may be conductive wires, e.g., a sensor conductor or thermocouple, or optical fibers. Additionally, a combination of conductive wires and optical fibers may be provided within the braid. The structural elements preferably provide a degree of torsional stiffness, kink resistance, or luminal rigidity to the catheter which is different than would otherwise be provided solely with one or more signal transmitting elements. The tubing wall is preferably a cross-linking polymer, such as polyimide matrix. In manufacture of the tubing, one or more layers of the polymer are coated on a mandrel and permitted to cure to form an inner layer of the tubing. The braid is then woven about the inner layer. Then, one or more layers of the polymer are coated over the braid and inner layer and permitted to cure to form an outer layer of the tubing which preferably forms a cross-linked and adhesive bond to the inner layer and provides a relatively homogenous structure.

36 Claims, 5 Drawing Sheets

FLEXIBLE TUBING WITH BRAIDED SIGNAL TRANSMISSION ELEMENTS

BACKGROUND OF THE INVENTION

1. Field of the Invention

This invention relates broadly to flexible polymer tubing having braided elements. This invention particularly relates to tubing having braided elements capable of carrying an electrical and/or optical signal.

2. State of the Art

Catheters are generally elongate flexible tubular devices intended to be inserted into body vessels, such as through the vascular system. It is well known to imbed wires in the wall of a catheter in order to impart torsional stiffness and kink resistance to the catheter, and structural rigidity sufficient to maintain an open lumen within the catheter. In addition, particular cardiovascular electrode catheters are used to electrically stimulate and/or monitor the heart, and in some cases, to modify the heart tissue. These catheters are provided with a signal transmitting element, e.g., a conductive element, extending a length of the catheter.

For example, U.S. Pat. No. 5,057,092 to Webster, Jr. discloses a catheter having a polymeric inner wall defining a central lumen for the passage of fluids or a guidewire therethrough, a reinforcing non-conductive braided mesh around the inner wall, and another polymeric outer wall about the braided mesh. Electrodes are provided at the distal end of the catheter, and a plurality of conductive wires extend the length of the catheter, coupled at their distal ends to the electrodes and couplable at their proximal ends to an electrostimulator or recorder. In one embodiment, the uninsulated conductive wires are built into the braided mesh. To prevent a short circuit, Webster, Jr. teaches that the conductive wires must run parallel within the braid, and not cross each other. As such, Webster, Jr. teaches that the conductive wires should be non-insulated and non-overlapping.

U.S. Pat. No. 5,630,806 to Inagaki et al. discloses a catheter having a inner layer defining a lumen, a spiral wound radiopaque reinforcement layer having one or more like spiral wound elements, each of which does not cross itself or overlap another. In one embodiment, the spiral wound elements are uninsulated conductors which permit the reinforcement layer to conduct signals as well as provide reinforcement. However, having the same elements function as both conductors and reinforcements is not particularly desirable as elements which provide the desired conductivity may not provide the desired reinforcement, and elements which provide the desired reinforcement may not provide the desired conductivity.

U.S. Pat. No. 5,591,142 to Van Erp discloses a catheter having a reinforcement braid made exclusively of like electrically conductive wires. The braid is located between two tubular layers of the catheter. The wires of the braid are separately insulated and grouped into at least two bundles which are then woven together, i.e., crisscrossed, about an inner layer of the catheter. Each of the wires of the braid can function as a conductor, and may be color coded to facilitate identifying the proximal and distal ends of particular conductors for coupling to sensor devices. However, such a design is limiting in that electrically conductive wires may not provide the most satisfactory reinforcement for a particular catheter. For example, in some situations, as recognized by U.S. Pat. No. 5,057,092 to Webster, Jr., discussed above, non-conductive braid elements may provide structural advantage for manipulating the catheter.

SUMMARY OF THE INVENTION

It is therefore an object of the invention to provide a flexible tubing having the capability of transmitting signals along its length and which also has desirable structural properties.

It is another object of the invention to provide a biocompatible medical-grade tubing for use in an electrode catheter.

It is a further object of the invention to provide a method of manufacturing tubing for use in an electrode catheter.

In accord with these objects, which will be discussed in detail below, a flexible preferably medical-grade tubing is provided which includes a wall made from a preferably biocompatible material and a plurality of braided elements forming a braid within the wall of the tube. The braided elements include one or more signal transmitting elements, and one or more metallic or non-metallic structural elements having structural properties different from the signal transmitting elements.

The biocompatible material is preferably a cross-link bonding polymer, and most preferably a polyimide matrix. In manufacture of the tubing, one or more layers of the polymer are coated on a mandrel and permitted to cure to form an inner layer of the tubing. The braid is then woven about the inner layer. Then, one or more layers of the polymer are coated over the braid and inner layer and permitted to cure to form an outer layer of the tubing which preferably forms a cross-linked and adhesion bond to the inner layer and provides a relatively homogenous structure. According to one preferred, but optional, aspect of the invention, one or more layers of the resin of the inner layer and/or the outer layer of the tubing is formed of a cross-linking polymer provided with polytetrafluoroethylene (PTFE) particles suspended therein such that the inner surface of the lumen, and/or the outer surface of the tubing, is lubricous. Furthermore, optionally, one or more layers of the resin of the tubing is formed of a cross-linking polymer provided with radiopaque, antimicrobial, antifungal, and/or antithrombotic particles suspended therein In one embodiment, the signal transmitting elements are conductive wires, e.g., a sensor conductor or thermocouple, which are electrically insulated. In another embodiment, the signal transmitting elements are optical fibers. Additionally, both conductive wires and optical fibers may be provided within the braid of the tubing. The structural elements are chosen to provide a degree of torsional stiffness, kink resistance, and/or luminal rigidity to the tubing which is different than would otherwise be provided solely with the signal transmitting elements. Each of the braid elements may have circular, non-circular, or substantially flat cross-sectional shapes.

With the above embodiments, the flexible tubing of the invention is particularly adapted for use in an electrode catheter, yet is versatile and capable of being used in other devices which require a relatively smaller diameter flexible tubing capable of transmitting a signal.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
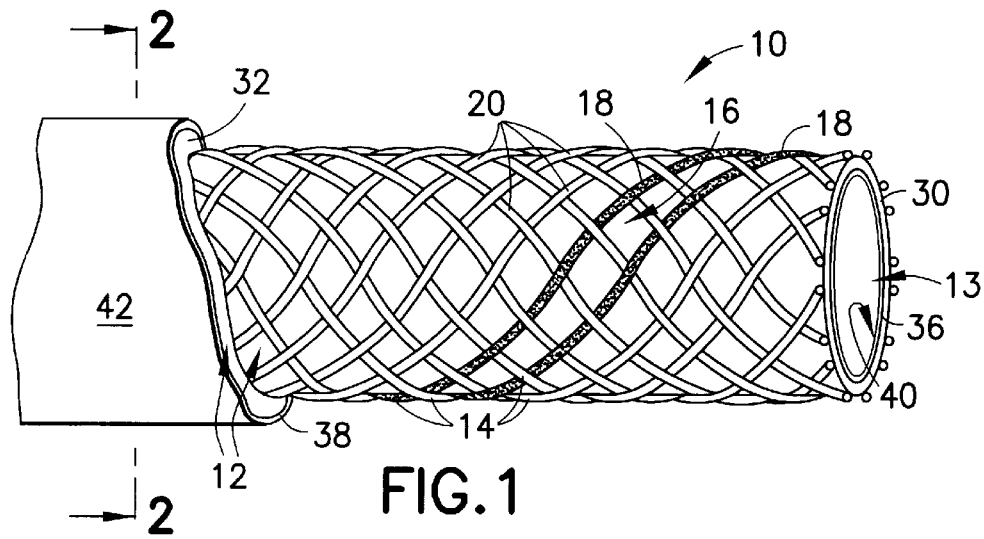
FIG. 1 is a broken partially cut-away perspective view of a flexible tubing according to a first embodiment of the invention.
Figure 2:
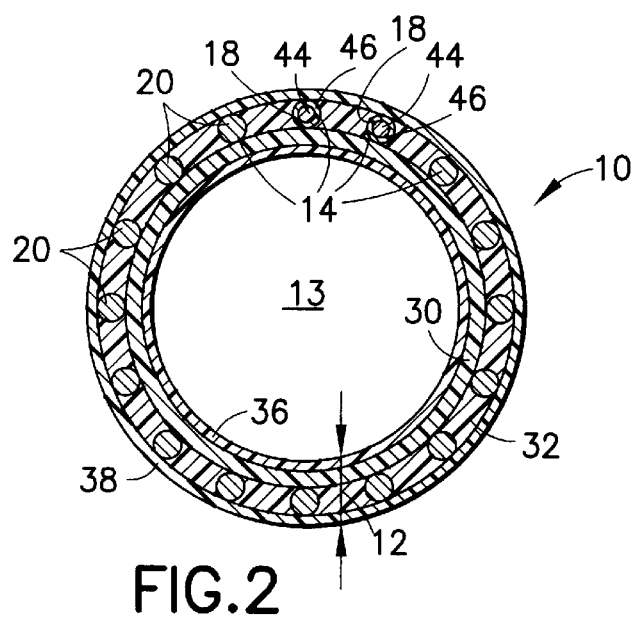
FIG. 2 is a section across line 2—2 in FIG. 1.

Turning now to FIGS. 1 and 2, a flexible preferably medical-grade tubing 10 according to the invention is shown. The tubing 10 includes a wall 12 defining a lumen 13, and is made from a biocompatible material. The tube is preferably sized to be inserted into the human vascular system. A plurality of braid elements 14 forming a braid 16 are provided within the wall of the tubing. The braid elements 14 include signal transmitting elements 18 and structural elements 20 having structural properties different from the signal transmitting elements. Preferably, there are sixteen braid elements 14 in total in the braid 16, with eight braid elements running helically parallel to each other and eight other braid elements running in an opposite direction helically parallel to each other such that they criss-cross the first eight braid elements and are woven therewith.

Figure 3:
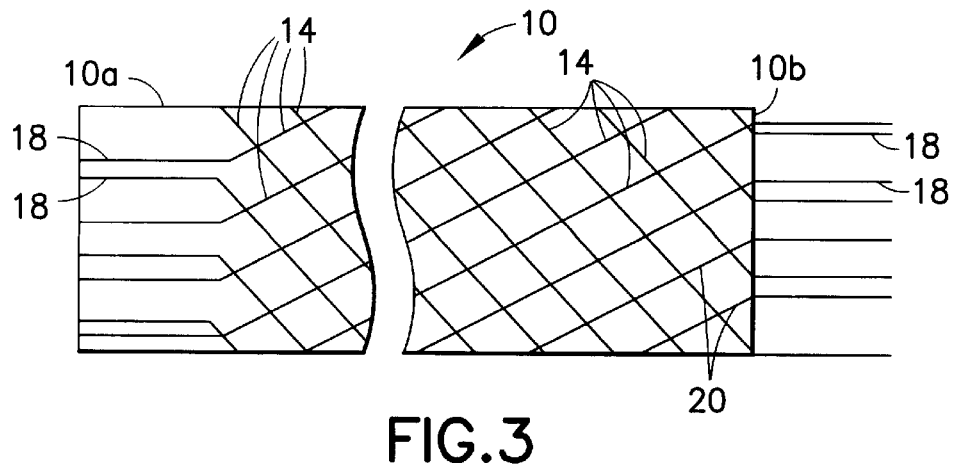
FIG. 3 is a broken schematic of the flexible tubing of the invention illustrating the longitudinal running braid elements at the ends of the tubing.

Referring now to FIG. 3, according to a preferred aspect of the invention, the braid elements 14 at end portions 10a, 10b of the tubing 10 are preferably not braided, running longitudinally in the wall 12, substantially parallel to the axis of the tubing 10. The end portions 10a, 10b preferably comprise the portions of the tubing 0.1 inch to 10 inches from the ends of the tubing. This design permits signal transmitting elements 18 of the braided elements 14 to be easily accessed and removed from the wall 12, stripped, and terminated. In FIG. 3, at end portion 10a, the braid elements 14 are shown located in the wall, while at end portion 10b, the braid elements are shown stripped of the wall of the tubing and any insulation, discussed below, about the elements.

Turning back to FIGS. 1 and 2, the biocompatible material of the wall 12 is preferably a cross-linking thermoset polymeric resin, and most preferably a polyimide matrix. A polyimide matrix is preferred because its break strength and elongation significantly exceed other thermoset materials. Furthermore, polyimide has a high dielectric strength, extreme resistance to reaction from other chemicals, a high operating temperature, can easily be bonded to medical grade adhesives, and does not degrade or break down when subjected to radiation-based sterilization methods. In addition, polyimide is extremely biocompatible. Nevertheless, other polymeric resins may alternatively or additionally be used in a polymeric resin mixture. For example, other suitable resins include polyurethane, polyester, polyamide, polyamidimide, and polytetrafluoroethylene.

In the manufacture of the tubing 10, a mandrel, such as an annealed copper wire, is provided having a diameter equivalent to the final diameter of the lumen 13 of the tubing 10. As such, the wire typically has a diameter between 0.002 inch to 0.100 inch, though mandrels of other diameters may be used. The mandrel is dipped into the polymeric resin to form a first sublayer of the polymer on the mandrel, which is then heated to cure the resin into a solid form. The process may be repeated to apply one or more additional sublayers (each preferably 0.00025–0.0005 inch thick) of the polymeric resin over the mandrel until a base (or inner) layer 30 of the wall 12 has a sufficient thickness, e.g., 0.0005 inch to 0.006 inch. Application of the polymer to the mandrel, the curing process, and other aspects of forming a tube over a mandrel are more completely disclosed in U.S. Pat. No. 5,630,806, which is hereby incorporated by reference herein in its entirety.

Once a base layer 30 of sufficient thickness is established, the braid elements 14, discussed in detail below, are braided (woven) about the base layer. Preferably, sixteen discrete braid elements 14 are separately braided over the base layer 30.

Then, one or more sublayers of the polymeric resin, each separately cured, are provided over the braid 16 and base layer 30 to form an encapsulating outer layer 32 of the wall 14. Each sublayer forms a cross-linked and mechanical adhesion bond to adjacent sublayers such that all the sublayers together, of both the base and outer layers form a relatively homogenous structure.

According to one preferred, but optional, aspect of the invention, one or more innermost sublayers 36 of the base layer 30 and/or outermost sublayers 38 of the outer layer 32 are comprised of the polymeric resin mixed with polytetrafluoroethylene (PTFE) particles, preferably one to fifteen percent by weight, suspended therein. The resulting base layer and outer layer, in a cured state, has PTFE particles on the surface such that the inner surface 40 of the wall 12 forming the lumen 13, and/or the outer surface 42 of the tubing 10 are lubricous. In addition, use of a polyimide/PTFE mixture for the innermost sublayers 36 of the base layer 30 permits the production of smaller diameter tubing. For smaller diameter tubing, a smaller diameter mandrel must be used. However, in the prior art, smaller mandrels tend to break prior to sufficient achieving elongation to be released from the plastic polyimide. The PTFE/polyimide mixture for the sublayers 36 of the base layer 30 reduces adhesion between the mandrel and the base layer and facilitates release of the mandrel from the tubing.

According to another optional aspect of the invention, one or more of the sublayers of the tube may be comprised of a thermoset polymeric resin, as listed above, in combination with particulate tungsten, barium and/or gold suspended therein. The particulates impart radiopacity to the tubing.

According to yet another optional aspect of the invention, one or more of the inner or outer sublayers of the tube may be comprised of a thermoset polymeric resin, as listed above, in combination with an antimicrobial or antifungal powder suspended therein. Exemplar antimicrobial powders include silver-ion producing agents, zinc-ion producing agents, and copper-ion producing agents. The antimicrobial or antifungal powder imparts the tubing with bactericide and/or fungicide properties.

According to a further optional aspect of the invention, one or more of the inner or outer sublayers of the tube may be comprised of a thermoset polymeric resin, as listed above, in combination with an antithrombotic powder suspended therein. Exemplar antithrombotic powders include powdered heparin, phosphorylcholine, ibuprofen, acetylsalicylic acid, indomethacin, prostaglandin, sulfinpyrazone, and warfarin. The antithrombotic powder suspended in the inner and/or outer layers of the tubing imparts the tubing with antithrombotic properties.

After the tubing wall 12 is completely formed, the mandrel is removed, preferably by stretching the mandrel to reduce its outer diameter, and then pulling the mandrel relative to the tubing 10. Finally, the lumen 13 is cleaned of metallic residue, preferably by flushing with an acidic solution, and dried. The tubing preferably has an outer diameter in the range of 0.008 inch to 0.15 inch.

Referring to FIGS. 1 and 2, according to a first embodiment of the invention, the two signal transmitting elements 18 are each comprised of a conductive wire 44, and an individual coating 46. The coating 46 is preferably formed from the same polymeric resin used to construct the wall 12, or another cross-link bonding thermoset resin. The coating process is preferably substantially the same as used to for a sublayer of the tubing on the wire mandrel. Use of a cross-link bonding resin coating 46 permits the coating to function as an electrical insulation for the wires 44, as a mechanical adhesion bonding agent, and as a cross-link bonding agent to bond the coating 46 with the layers 30, 32 of the wall 12. The coating 46 on each conductive wire 44 is preferably distinctly colored from the others for ease of recognition of the respective wires, particularly when coupling electrodes and sensors thereto. The conductive wires 44 are preferably made from ETP copper, OF copper, cryogenic copper, silver-plated copper, nickel-plated copper, copper-nickel alloys such as constantan or Inconel™, other copper alloys, aluminum, silver, gold, platinum or rhodium. The structural elements 20 may be made from metallic and/or non-metallic materials. For example, suitable metallic materials include stainless steel and nickel-titanium alloy, preferably having a diameter range from 0.00062 inch to 0.005 inch. Suitable non-metallic materials include nylon, polyester, polypropylene, fiberglass, cotton, aramid fibers, e.g., those sold under the trademarks Kevlar™ and Nomex™, and polyester films, e.g., those sold under the trademark Mylarm, preferably having a diameter range from 0.0005 inch to 0.004 inch. The structural elements 20 are harder and less malleable than the conductive wires 44. Therefore, the described structural elements 20 provide a tubing construction which has greater tensile strength and increased toughness relative to the prior art tubing with conductive elements only. In addition, the described structural elements 20 makes the tubing 10 less subject to deformation. Each of the braid elements 14, whether conductive wires 44 or structural elements 20, may have circular, non-circular, or substantially flat cross-sectional shapes.

According to the first embodiment, the coated conductive wires are braided with the structural elements 20, preferably such that the coated conductive wires 44 run helically parallel to each other. The resulting braid 16, preferably in which the structural elements 20 criss-cross each other in the braid, provides a degree of torsional stiffness, kink resistance, luminal rigidity, tensile and compressive strength, hoop strength and scrape resistance to the tubing 10 which is different and more desirable than would otherwise be provided solely with a braid containing conductive wires only. Additionally, more than two conductive wires may be provided, with each of the conductive wires extending in a helical path parallel to the paths of the other conductive wires.

Figure 4:
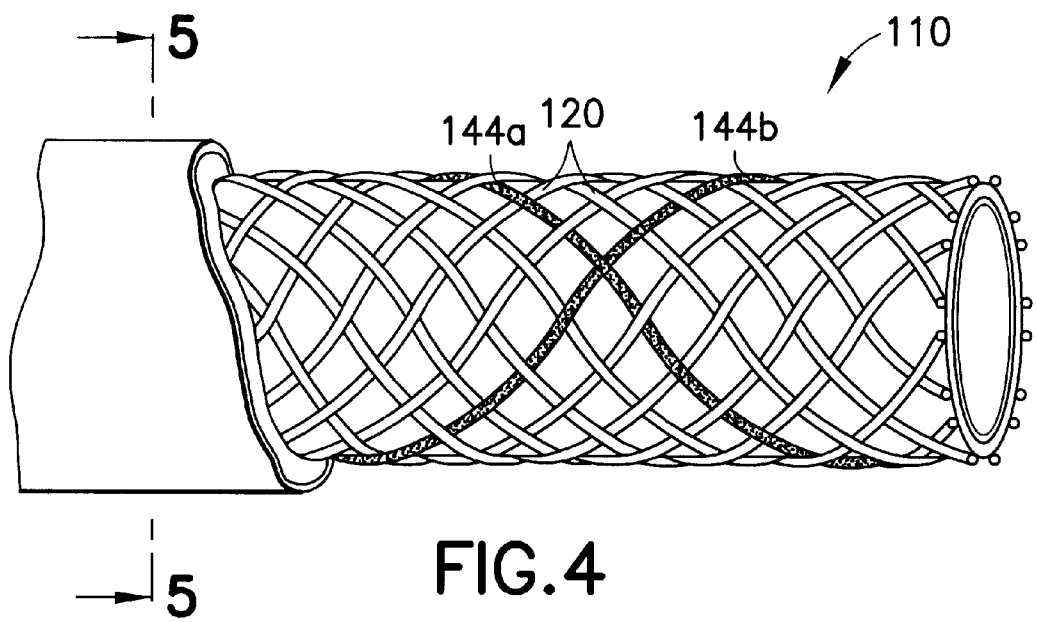
FIG. 4 is a broken partially cut-away perspective view of a flexible tubing according to a second embodiment of the invention.
Figure 5:
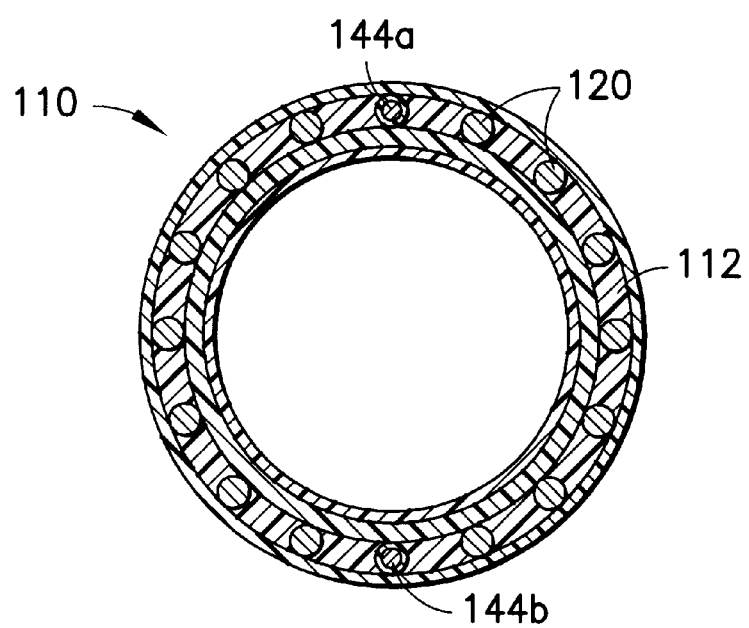
FIG. 5 is a section across line 5—5 in FIG. 4.

Turning now to FIGS. 4 and 5, a second embodiment of the tubing 110 of the invention, generally similar to the first embodiment, is shown. The second embodiment includes two conductive wires 144a, 144b which are coated with coatings 146a, 146b and braided with the structural elements 120 such that the conductive wires are braided in opposite helical paths relative to each other and criss-cross each other.

Figure 6:
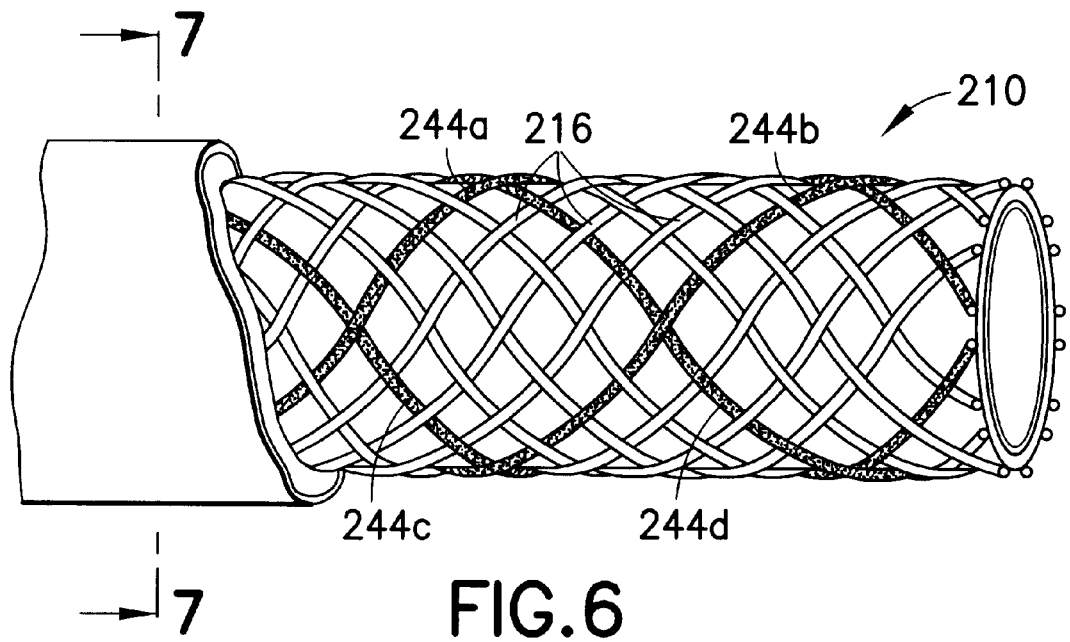
FIG. 6 is a broken partially cut-away perspective view of a flexible tubing according to a third embodiment of the invention.
Figure 7:
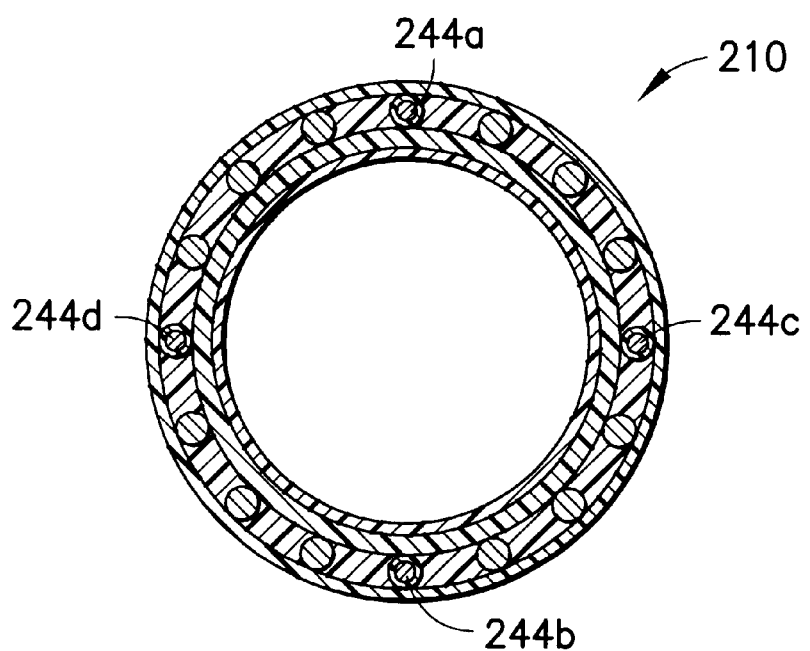
FIG. 7 is a section across line 7—7 in FIG. 6.

Referring now to FIGS. 6 and 7, in a third embodiment, more than two (e.g., four) conductive wires 244a, 244b, 244c, 244d which are separately coated by coatings 246a, 246b, 246c, 246d are provided in the braid 216 of the tubing 210. Two of the conductive wires 244a, 244b extend in a helical path opposite the other conductive wires 244c, 244d.

Figure 8:
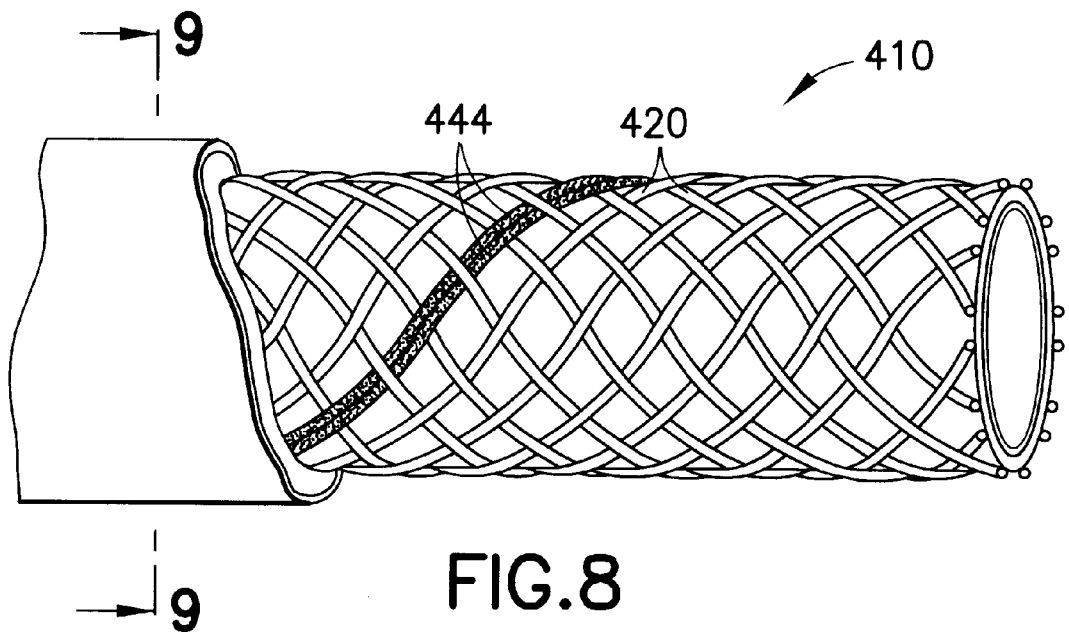
FIG. 8 is a broken partially cut-away perspective view of a flexible tubing according to a fifth embodiment of the invention.
Figure 9:
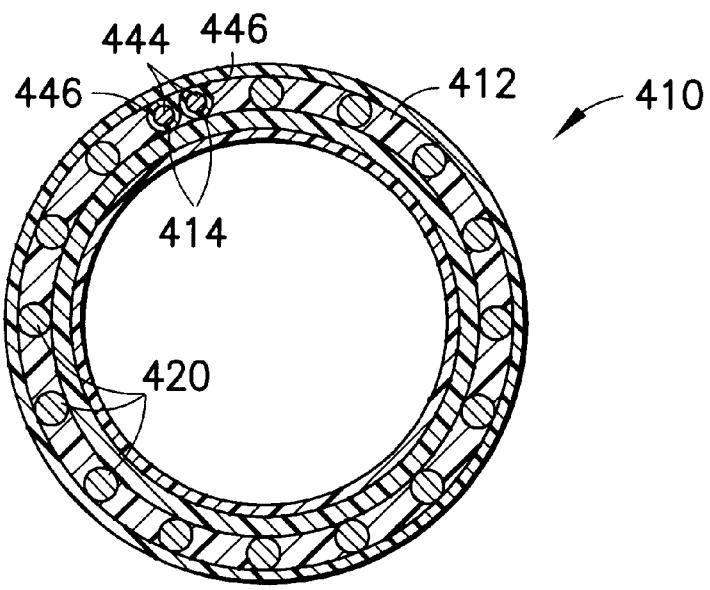
FIG. 9 is a section across line 9—9 in FIG. 8.

Turning now to FIGS. 8 and 9, in a fourth embodiment of the invention, two elements 414 of the braid of the tubing 410 are thermocouples 444, extending in helically parallel and adjacent paths through the tubing wall 412. The thermocouples 444 are preferably of B, C, E, J, K, N, R, S or T type. The thermocouple 444 is preferably coated in a cross-link bonding thermoset resin insulation 446. Remaining elements of the braid 416 are preferably structural elements 420.

Figure 10:
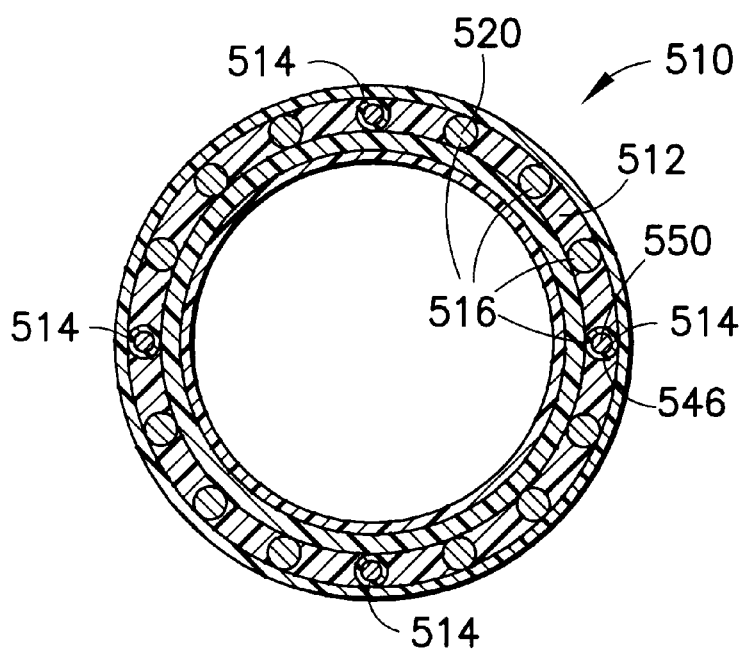
FIG. 10 is a section view of a sixth embodiment of the invention.

Referring now to FIG. 10, in a fifth embodiment of the invention, each signal transmitting element 514 in the tubing 510 is an optic fiber 550 which may be individually coated in a colored cross-link bonding thermoset resin coating 546 to provide easy identification and increased stability within the tubing wall 512. The braid 516 contains structural elements 520 in addition to the optic fibers.

Figure 11:
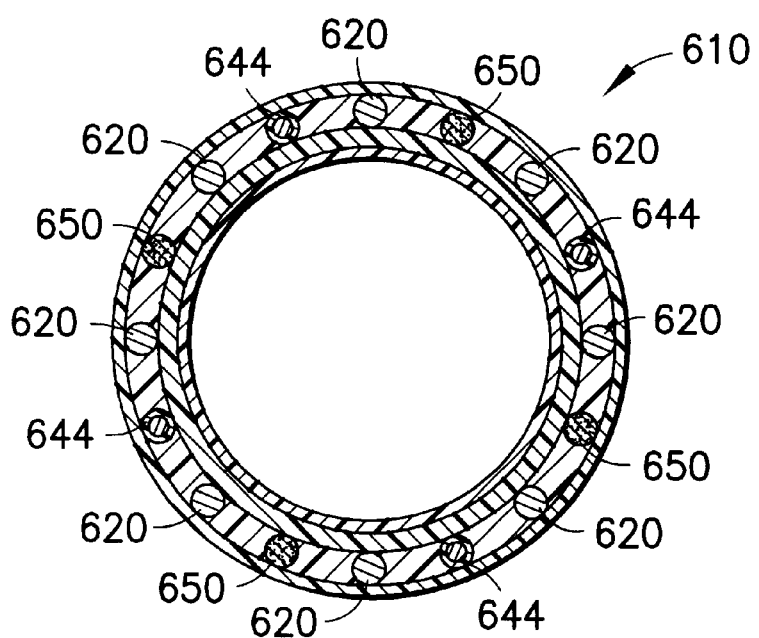
FIG. 11 is a section view of a seventh embodiment of the invention.

Turning now to FIG. 11, in a sixth embodiment of the invention, the tubing 610 is provided with a braid which includes both conductive wires 644 and optic fibers 650, in combination with structural elements 620.

With the above embodiments, the flexible tubing of the invention is particularly adapted for use in an electrode catheter, yet is versatile and capable of being used in other devices which require a relatively smaller diameter flexible tubing capable of transmitting a signal.

There have been described and illustrated herein several embodiments of a flexible tubing provided with signal transmitting elements. While particular embodiments of the invention have been described, it is not intended that the invention be limited thereto, as it is intended that the invention be as broad in scope as the art will allow and that the specification be read likewise. Thus, while particular polymeric resins have been disclosed, it will be appreciated that other flexible, preferably biocompatible, and preferably cross-link bonding polymers can be used as well. Furthermore while particular types of signal transmitting elements and structural elements have been disclosed, it will be understood that other such elements can be used. It will therefore be appreciated by those skilled in the art that yet other modifications could be made to the provided invention without deviating from its spirit and scope as so claimed.

What is claimed is:

1. A flexible tube for use as a medical electrode catheter, comprising:
   a) an inner wall layer comprising a polyimide matrix and defining a lumen;
   b) a plurality of braid elements forming a braid over a length of said inner wall layer, said braided elements including,
      i) at least two signal transmitting elements, each said signal transmitting element being individually coated in a coating, said signal transmitting elements criss-crossing each other within said braid, and
      ii) at least one non-conductive element having a strength greater than said signal transmitting elements; and
   c) an outer wall layer of said polyimide matrix over said plurality of braided elements.

2. A flexible tube according to claim 1, wherein:
said inner layer and said outer layer are cross-link bonded to each other.

3. A flexible tube according to claim 1, wherein:
said coating is formed from said polyimide matrix.

4. A flexible tube according to claim 1, wherein:
said signal transmitting elements are electrical conductors.

5. A flexible tube according to claim 1, wherein:
said coating is distinctly colored for each of said signal transmitting elements.

6. A flexible tube according to claim 1, wherein:
said at least two signal transmitting elements are optic fibers.

7. A flexible tube according to claim 1, wherein:
said at least two signal transmitting elements include at least one electrical conductor and at least one optic fiber.

8. A flexible tube according to claim 1, wherein:
said polyimide matrix of at least one of said inner layer and said outer layer includes PTFE particles suspended therein.

9. A flexible tube according to claim 1, wherein:
said polyimide matrix of at least one of said inner layer and said outer layer includes radiopaque particles suspended therein.

10. A flexible tube according to claim 1, wherein:
said polyimide matrix of at least one of said inner layer and said outer layer includes at least one of antimicrobial and antifungal particles suspended therein.

11. A flexible tube according to claim 1, wherein:
said polyimide matrix of at least one of said inner layer and said outer layer includes antithrombotic particles suspended therein.

12. A flexible tube according to claim 1, wherein:
said flexible tube has a longitudinal axis and includes an end portion at which at least one of said plurality of braid elements extends substantially parallel to said axis.

13. A flexible tube, comprising:
a) an inner wall layer comprising a polymide resin and defining a lumen;
b) a plurality of unbundled braid elements woven in a braid over a length of said inner wall layer, said braid elements including at least one signal transmitting element and at least one structural element having a structural property different than said at least one said signal transmitting element; and
c) an outer wall layer of said polymide resin over said plurality of braid elements, said outer wall layer being cross-linked bonded with said inner wall layer.

14. A flexible tube according to claim 13, wherein:
said signal transmitting elements are electrically conductive and each individually covered in an insulative coating.

15. A flexible tube according to claim 14, wherein:
said insulative coating for each of said signal transmitting elements is comprised of said polymer resin.

16. A flexible tube according to claim 14, wherein:
said insulative coating for each of said signal transmitting elements is distinctly colored.

17. A flexible tube according to claim 13, wherein:
said signal transmitting elements are optical fibers.

18. A flexible tube according to claim 13, wherein:
said signal transmitting elements extend helically parallel to each other.

19. A flexible tube according to claim 13, wherein:
at least one of said signal transmitting elements crisscrosses another of said signal transmitting elements.

20. A flexible tube according to claim 13, wherein:
said polyimide of at least one of said inner layer and said outer layer includes PTFE particles suspended therein.

21. A flexible tube according to claim 13, wherein:
said polyimide of at least one of said inner layer and said outer layer includes radiopaque particles suspended therein.

22. A flexible tube according to claim 13, wherein:
said polyimide of at least one of said inner layer and said outer layer includes at least one of antimicrobial and antifungal particles suspended therein.

23. A flexible tube according to claim 13, wherein:
said polyimide of at least one of said inner layer and said outer layer includes antithrombotic particles suspended therein.

24. A flexible tube accroding to claim 13, wherein:
said flexible tube has a longitudinal axis and includes an end portion at which at least one of said plurality of braid elements extends substantially parallel to said axis.

25. A flexible tube, comprising:
a) an inner wall layer comprising a polyimide matrix and defining a lumen;
b) a plurality of unbundled braid elements separately woven in a braid over a length of said inner wall layer, said braid elements including at least one signal transmitting element and at least one structural element having a property different than said at least one signal transmitting element; and
c) an outer wall layer of said polyimide matrix over said plurality of braid elements, said outer wall layer being cross-linked bonded with said inner wall layer.

26. A flexible tube according to claim 25, wherein:
said plurality of braid elements includes signal transmitting elements.

27. A flexible tube according to claim 26, wherein:
said signal transmitting elements include conductive wires.

28. A flexible tube according to claim 27, wherein:
said conductive wires having a coating formed of said polyimide, and said inner wall layer and said outer wall layer are cross-linked bonded with said coating.

29. A flexible tube according to claim 26, wherein:
said signal transmitting elements include optic fibers.

30. A flexible tube according to claim 26, wherein:
said plurality of braid elements includes structural elements having structural properties different than said signal transmitting elements.

31. A flexible tube according to claim 25, wherein:
said polyimide of at least one of said inner layer and said outer layer includes PTFE particles.

32. A flexible tube according to claim 25, wherein:
said polyimide of at least one of said inner layer and said outer layer includes radiopaque particles suspended therein.

33. A flexible tube according to claim 25, wherein:
said polyimide of at least one of said inner layer and said outer layer includes at least one of antimicrobial and antifungal particles suspended therein.

34. A flexible tube according to claim 25, wherein:
said polyimide of at least one of said inner layer and said outer layer includes antithrombotic particles suspended therein.

35. A flexible tube accroding to claim 25, wherein:
said flexible tube has a longitudinal axis and includes an end portion at which at least one of said plurality of braid elements extends substantially parallel to said axis.

36. A flexible tube according to claim 25, wherein:
said tube is sized to be inserted into through the vascular system.

* * * * *